United States Patent
Risher-Kelly

(10) Patent No.: US 8,274,532 B2
(45) Date of Patent: Sep. 25, 2012

(54) SYSTEM FOR ADAPTIVELY ORIENTING A DISPLAY IMAGE ON A DEVICE

(75) Inventor: Clifford Risher-Kelly, Wells, ME (US)

(73) Assignee: Draeger Medical Systems, Inc., Andover, MA (US)

( * ) Notice: Subject to any disclaimer, the term of this patent is extended or adjusted under 35 U.S.C. 154(b) by 684 days.

(21) Appl. No.: 12/447,570

(22) PCT Filed: Nov. 6, 2007

(86) PCT No.: PCT/US2007/083751
§ 371 (c)(1),
(2), (4) Date: Apr. 28, 2009

(87) PCT Pub. No.: WO2008/060897
PCT Pub. Date: May 22, 2008

(65) Prior Publication Data
US 2010/0053218 A1     Mar. 4, 2010

(51) Int. Cl.
G09G 5/00 (2006.01)
G09G 5/08 (2006.01)
G06F 3/02 (2006.01)
G06F 3/033 (2006.01)

(52) U.S. Cl. ......... 345/649; 345/158; 345/156; 345/172

(58) Field of Classification Search .................. None
See application file for complete search history.

(56) References Cited

U.S. PATENT DOCUMENTS

| | | |
|---|---|---|
| 4,267,555 A | 5/1981 | Boyd et al. |
| 5,808,254 A | 9/1998 | Wu |
| 5,949,408 A | 9/1999 | Kang et al. |
| 6,556,183 B1 * | 4/2003 | Gartrell et al. ............... 345/156 |
| 6,952,601 B2 * | 10/2005 | Lieu et al. .................. 455/575.1 |
| 6,956,564 B1 * | 10/2005 | Williams ....................... 345/179 |
| 7,181,251 B2 * | 2/2007 | Stohr et al. .................... 455/566 |

(Continued)

FOREIGN PATENT DOCUMENTS

CN    1689039 A    10/2005

(Continued)

OTHER PUBLICATIONS

Office Action for corresponding Chinese Application No. 200780041766.2 dated Jun. 17, 2011.

*Primary Examiner* — Kee M Tung
*Assistant Examiner* — Zhengxi Liu
(74) *Attorney, Agent, or Firm* — Jack Schwartz and Associates, PLLC

(57) ABSTRACT

A system adaptively orients a display image on a device for presenting data acquired via one or more cables connected to a particular side of the device. The system includes a sensor for detecting orientation of the device and providing a device orientation representative signal indicating whether the device is in a first orientation or a second orientation substantially different to the first orientation. A display screen presents display images on the device. A display generator automatically generates a display image on the display screen oriented to be upright in the first and second orientations of the device, in response to the orientation representative signal. A command processor adaptively selects functions assigned to user selectable buttons positioned on both sides of the display screen of the device, in response to the orientation representative signal.

12 Claims, 2 Drawing Sheets

U.S. PATENT DOCUMENTS

| | | |
|---|---|---|
| 2002/0140675 A1 | 10/2002 | Ali et al. |
| 2004/0201595 A1 | 10/2004 | Manchester |
| 2006/0238517 A1 | 10/2006 | King et al. |
| 2006/0287015 A1* | 12/2006 | Dunko .................. 455/575.4 |
| 2007/0004451 A1* | 1/2007 | Anderson ................ 455/556.1 |
| 2008/0062134 A1* | 3/2008 | Duarte et al. ................ 345/169 |

FOREIGN PATENT DOCUMENTS

| | | |
|---|---|---|
| EP | 0 114 253 | 8/1984 |
| EP | 0 431 581 | 6/1991 |
| EP | 1 547 011 B1 | 6/2005 |
| WO | WO/2005/089834 | 9/2005 |
| WO | WO/2005/093550 | 10/2005 |

\* cited by examiner

SYSTEM FOR ADAPTIVELY ORIENTING A DISPLAY IMAGE ON A DEVICE

FIELD OF THE INVENTION

The present invention relates to devices which display images, and in particular to devices which display images while being operated in different orientations.

BACKGROUND OF THE INVENTION

Medical devices, in particular medical devices which are patient monitoring and/or treatment devices, include or operate with cables, hoses, tubes, etc. which are connected between the medical device and the patient. These must be long enough to reach from the medical device to the appropriate locations on the patient. However, if they are too long, they are obtrusive and hazardous because they may kink, tangle, become entwined with the patient, interfere with the healthcare worker, become snagged on that worker's clothes, and during patient transport, may become snagged or tangled with external obstructions. On the other hand, if they are too short, they require that the medical device be placed at a particular location and in a particular orientation with respect to the patient. This location and orientation, however, may interfere with access by healthcare workers to the patient. In short, device location and orientation is often constrained by the attached cables, hoses, tubes, etc.

In an effort to minimize these effects, the medical device may be physically rotated to permit the cables to run in a more optimal manner. Physically smaller medical devices may be easily rotated, but are usually more constrained in their use. That is, smaller medical devices generally perform fewer and/or more limited functions. Physically larger medical devices may perform a relatively wider range of functions, but are harder to rotate. Further, rotating the medical device causes the image displayed on the display device to also be rotated. This makes the image harder to read and any graphical image (e.g. EKG, respiration or similar waveforms) harder to evaluate by healthcare workers.

Some medical devices further include buttons which a user may press to invoke a desired function. Some such medical devices locate the buttons near the edge of the display screen. The display screen displays respective labels near the buttons to inform the user what function is associated with the respective buttons. This allows the buttons to be dynamically reassigned to different functions by changing the image displayed on the display screen. As described above, however, if a medical device is rotated, the labels related to the buttons may become hard to read. In addition, the location of the buttons activated to perform frequently performed functions is changed. That is, a button on the upper left corner of the medical device when the medical device is oriented in a normal manner becomes the button on the lower right corner of the medical device if the medical device is inverted. This means that a healthcare worker used to pressing the upper left button to perform a frequently desired function may, when the medical device is inverted, accidentally press the upper left button which, as described above, is associated with a different function than that desired.

Display systems which operate in different orientations have been developed. Such systems permit the display system to be used in several orientations. For example, the display system may be either mounted under a cupboard with the display screen rotated downward for use in, for example, a kitchen; or to be placed atop a counter with the display screen rotated upward for use on, for example, a desktop; or to be placed partially opened on its side. An orientation switch, which may be an automatic orientation switch, in such a system conditions the electronics driving the display screen to display the image in the proper orientation in any of the positions.

BRIEF SUMMARY OF THE INVENTION

In accordance with principles of the present invention, a system adaptively orients a display image on a device for presenting data acquired via one or more cables connected to a particular side of the device. The system includes a sensor for detecting orientation of the device and providing a device orientation representative signal indicating whether the device is in a first orientation or a second orientation substantially different to the first orientation. A display screen presents display images on the device. A display generator automatically generates a display image on the display screen oriented to be upright in the first and second orientations of the device, in response to the orientation representative signal. A command processor adaptively selects functions assigned to user selectable buttons positioned on both sides of the display screen of the device, in response to the orientation representative signal.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, display device system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

Figure 1:
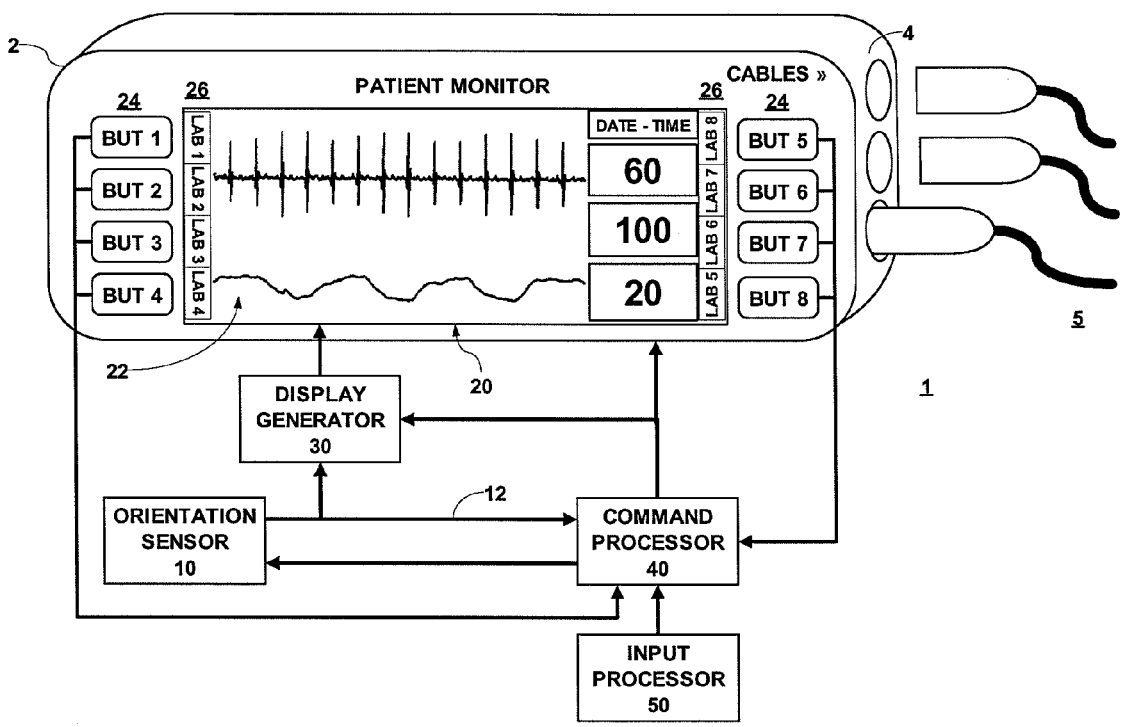
FIG. 1 is a diagram partially in block form and partially in orthogonal form of a system according to principles of the present invention.

FIG. 1 is a diagram, partially in block form and partially in orthogonal form, of a system 1 according to principles of the present invention. The system 1 of FIG. 1 adaptively orients a display image 22 on a device 2 for presenting data acquired via one or more cables 5 connected to a particular side 4 of the device 2. The system 1 includes a sensor 10 for detecting orientation of the device 2 and providing a device orientation representative signal 12 indicating whether the device 2 is in a first orientation or a second orientation substantially different to the first orientation. Operation of the sensor 10 is described in more detail below. A display screen 20 presents display images 22 on the device 2. A display generator 30 automatically generates a display image 22 on the display screen 20 oriented to be upright in the first and second orientations of the device 2, in response to the orientation representative signal 12. A command processor 40 adaptively selects functions assigned to user selectable buttons 24 positioned on both sides of the display screen 20 of the device 2, in response to the orientation representative signal 12. In an embodiment of the invention of FIG. 1, an input processor 50 receives user entered data selecting an image orientation and overriding the sensor 10 detected orientation.

Referring to a medical electronic device, the system 1 of FIG. 1 adaptively orients a display image 22 on a device 2 for presenting patient medical parameters acquired via one or more cables 5 connected to a particular side 4 of the device 1. The system 1 includes a sensor 10 for detecting the orientation of the device 2 and provides a device orientation representative signal 12 indicating whether the device 2 is in a first orientation or a second orientation substantially different to the first orientation. A display screen 20 presents a display image 22 on the device 2. A display generator 30 automatically generates a display image 22 on the display screen 20 oriented to be upright in the first and second orientations of the device 1, in response to the orientation representative signal 12. A command processor 40 adaptively selects functions assigned to user selectable buttons 24 positioned on both sides of the display screen 20 of the device 2, in response to the orientation representative signal 12.

In one embodiment, the user selectable buttons 24 are substantially symmetrically positioned on both sides of the display screen 20. In another embodiment, the one or more cables 5 convey patient data, and in particular patient physiological signals, from patient attached sensors (not shown) to the device 2.

More specifically, the command processor 40 executes an executable application which controls the operation of the device 2. This includes executing executable procedures for receiving physiological signals from the cables 5 connected to the patient, generating medical parameter data from the physiological signals, and conditioning the display generator 30 to generate image representative signals which condition the display screen 20 to display the medical parameter data in an appropriate manner. For example, some medical parameters may be displayed in graphical form, such as the EKG waveform signal displayed near the top of the display screen 20 and the respiration waveform signal displayed near the bottom of the display screen 20. Other medical parameter data may be displayed in numerical form, such as heart rate, $SpO_2$, respiration rate, etc.

The device 2 may also perform functions selected by a user. For example, a user may desire to perform a reset function, which would reset all stored medical parameter data and restart collection of such data; or a user may wish to display medical parameter trends instead of instantaneous parameters; or a user may wish to record the medical parameters at the present time due to an observed event, or some other patient interaction. Further, performing one function may permit different functions to be available for selection by a user. For example, invoking the trends function, described above, may allow user access to a function for changing the trend calculation parameters, or to functions for allowing the user to follow the trend data over a wider time range than is displayable on the available size of the display screen 20, e.g. 'forward' and 'back' functions may be provided to allow a user to traverse the trend data.

A user may activate one of the user selectable buttons 24 to invoke a desired function. The command processor 40 in the device 2 conditions the display generator 30 to display an image 22 on the display screen 20 including labels 26, e.g. "LAB 1", "LAB 2", . . . , "LAB 8" adjacent to the associated user selectable buttons 24, e.g. "BUT 1", "BUT 2", . . . , "BUT 8", respectively. In an actual embodiment, the displayed labels 26 provide an indication to the user of which function is invoked by activation of the associated adjacent button 24, e.g. "ZeroAll", "Trends", etc. and/or "ChgParms", "Forward", "Back", etc. during 'Trend' displays.

The command processor 40 receives signals from the user selectable buttons 24 which enable the command processor 40 to detect the activation of a particular user selectable button 24. In response to detecting the activation of a particular user selectable button 24, the command processor 40 executes the executable procedure for performing the function associated with the detected particular user selectable button 24. One skilled in the art understands that a single user selectable button 24 may invoke different functions at different times depending on prior invocations of functions by the user, and that the labels 26 are dynamically changed by the command processor 40 and display generator 30, to correspond to the function currently invoked by activation of the associated user selectable button 24.

One skilled in the art also understands that the indicia "BUT 1" through "BUT 8" are illustrated in FIG. 1 for increased understanding of the figure. These indicia would not appear on the buttons 24 in an actual embodiment of the invention. Instead, the buttons would typically be blank. One skilled in the art further understands that, although the labels 26 are illustrated in FIG. 1 as being oriented vertically, they may be displayed in any size and/or orientation, may include text or images such as icons, may include emphasis such as larger type or images or different color(s), or any combination of the these sufficient to inform the user of the function invoked by activation of the associated button 24.

Figure 2:
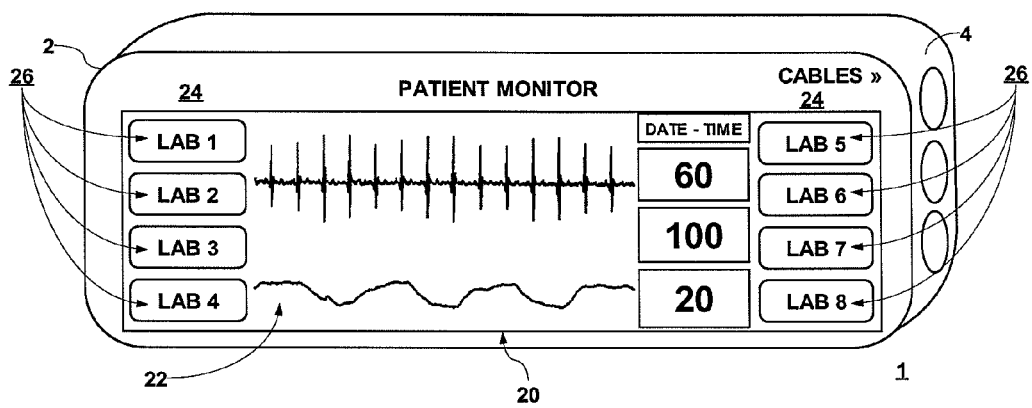
FIG. 2 is a diagram in orthogonal form illustrating a portion of another embodiment of a system according to principles of the present invention.

In the embodiment illustrated in FIG. 1, the user selectable buttons 24 are physical push buttons, and the labels 26 are displayed on the display screen 20 adjacent the associated button 24, as described above. FIG. 2 is a diagram in orthogonal form of a portion of another embodiment of a system 1 according to the present invention. In FIG. 2, those elements which are the same as those illustrated in FIG. 1 are designated by the same reference number and are not described in detail.

In FIG. 2, the display screen 20 is a touch sensitive screen. In FIG. 2, the user selectable buttons 24 are implemented as touch screen buttons on the display screen 20. The touch screen buttons 24 are displayed as surrounded by a boundary which is a rounded rectangle. In FIG. 2, the touch screen buttons 24 images further include the associated label 26 within the illustrated boundaries of the button 24. A user selectable button 24 is activated by the user by touching the display screen 20 within the boundary of that button 24. In response to activation of a user selectable button 24 in this manner, the command processor 40 invokes the associated function, as described above. One skilled in the art understands that the boundary of a touch screen button 24 may be any shape that enables the user to activate that button 24. One skilled in the art further understands that the labels 26 may instead be displayed beside the buttons 24 in the manner similar to that illustrated in FIG. 1 while the buttons 24 may be illustrated as blank shapes, such as rounded rectangles, similar in appearance to physical buttons.

Figure 3:
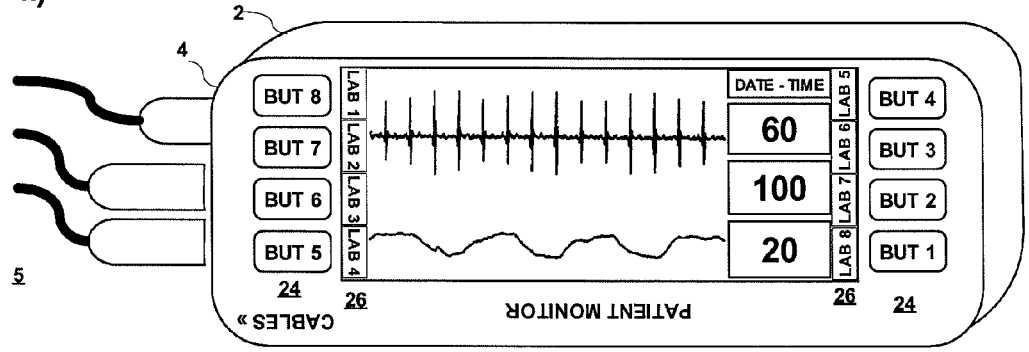
FIG. 3 is a diagram in orthogonal form illustrating the operation of a system as illustrated in FIG. 1 and/or FIG. 2 in a different orientation.
Figure 3:
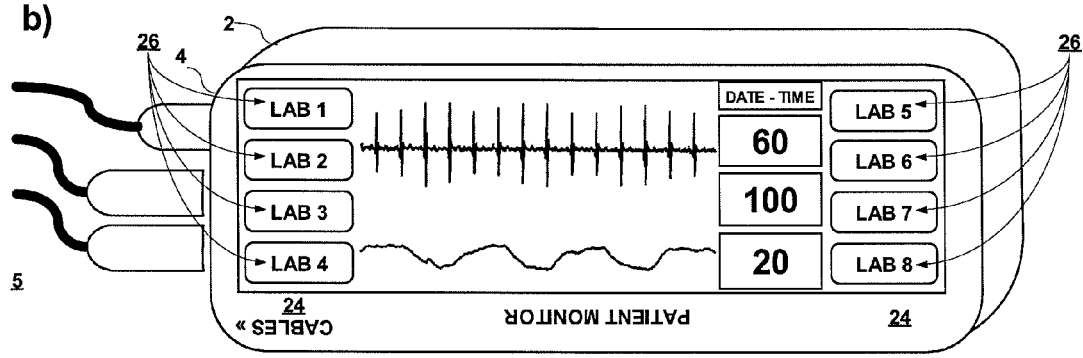

FIG. 3 is a diagram in orthogonal form illustrating the operation of a system 1 as illustrated in FIG. 1 and/or FIG. 2 in a second, different orientation. The second orientation in FIG. 3 is at least one of: (a) substantially upside down relative to the first orientation, and/or (b) rotated substantially 180 degrees relative to the first orientation in FIG. 1. FIG. 3a corresponds to the embodiment of FIG. 1 and FIG. 3b corresponds to the embodiment of FIG. 2. In FIG. 3 a and b, those elements which are the same as those illustrated in FIG. 1 and FIG. 2 are designated by the same reference number and are not discussed in detail below. In FIG. 3 a and b, the orientation of device 2 is inverted relative to the orientation of the device 2 in FIG. 1 and FIG. 2. This may be seen by the indicia "PATIENT MONITOR" and "CABLES>>" on the device appearing inverted. In addition, the cables 5, connected to the particular side 4 of the device 2 now are connected to the left side of the device 2 instead of the right side as in FIG. 1.

Referring to the block diagram of the system 1 illustrated in FIG. 1 in conjunction with the orthogonal illustrations of the device 2 in FIGS. 3a and b, the orientation sensor 10 detects the orientation of device 2 and generates a device orientation representative signal 12 indicating the orientation of the device 2: i.e. normal or inverted. The orientation sensor 10 may be a physical switch operated by a user. However, in one embodiment, the orientation sensor 10 may be a sensor which automatically detects the orientation of the device 2.

In one such embodiment, the orientation sensor 10 senses rotation of the device 2 around three axes. A first axis runs vertically through the center of the device 2. Rotation around this axis causes the left side of the device 2 to rotate out of the page and the right side to rotate into the page, and visa-versa (yaw). Because this rotation does not change the orientation of the display image 22, data representing rotation about this axis is not further processed to determine the orientation of the device 2.

A second axis runs horizontally through the device 2 from back to front. Rotation about this axis causes the left side of the device 2 to go down and the right side of the device 2 to go up and visa-versa (roll), like rotating the hands of a clock or propeller of an airplane. The orientation of the device 2 about this axis is detected. When the device 2 passes through the 90 degree orientation, corresponding to the device 2 being oriented on its side, i.e. with the particular side 4 being at the bottom or top, the orientation sensor 10 generates an orientation representative signal 12 indicating whether the orientation of the device 2 is normal or inverted, as appropriate. In one embodiment, hysteresis is introduced into the orientation representative signal 12 to prevent rapid changes back and forth as the device 2 rotates through the 90 degree point.

A third axis runs horizontally through the device 2 from side to side. Rotation in this axis causes the top of the device 2 to come out of the page and the bottom of the device 2 to go into the page, and visa-versa (pitch). The orientation of the device 2 about this axis is also detected. When the device 2 passes through the 90 degree orientation, corresponding to the display screen 20 facing down or up, this corresponds to a change in orientation. However, because the display screen 20 is nearly flat at this point in the rotation, there is no clear "up" or "down" which may be detected by the orientation sensor 10. Consequently, at this point of the rotation, the orientation representative signal 12 may oscillate between indicating an upright and upside down orientation rapidly, making the device 2 useless. In one embodiment, when the orientation sensor 10 detects that the device 2 is in the neighborhood of the 90 degree point in the rotation, i.e. the display screen 20 is facing up or down, the orientation representative signal 12 is frozen, i.e. maintained in the previous state. It remains frozen until the device 2 is rotated to an angle outside of the neighborhood around 90 degrees. In more detail, when the rotation is within 30 degrees of being flat, the orientation representative signal is frozen. When the rotation of the device 2 goes beyond the 30 degree neighborhood, the orientation sensor 10 detects whether the device 2 is in normal or inverted orientation and generates an orientation representative signal accordingly.

In short, the orientation sensor 10 processes sensed rotation around at least two axes to provide the orientation representative signal 12 indicating whether the device 2 is in the first or second orientation (i.e. normal or inverted).

Such an orientation sensor 10 may instead be an acceleration detector arranged to detect the acceleration due to gravity, or may be other such detectors such as mercury switches, etc. One skilled in the art understands that any such detector may be used provided it automatically generates a signal indicating the present orientation of the device 2.

Referring to FIGS. 3a and b, the orientation sensor 10 generates a device orientation representative signal 12 indicating that the device 2 is inverted. In response, the display generator 30 generates an image representative signal for the display screen 20 which will cause the display screen 20 to display an image 22 which is upright in the currently detected orientation.

Referring more specifically to FIG. 3a, the display image 22 of the medical parameters is upright, even though the display screen 20 of the device 2 is inverted. This permits the displayed EKG and respiration waveforms to be more easily and accurately interpreted by a healthcare worker. The numeric medical parameters are also displayed in an upright orientation, making them easy to read.

In FIG. 1, button 24 "BUT 1" is on the upper left side of the device 2. The label 26 "LAB 1" is associated with the button 24 "BUT 1". In an actual embodiment, that label may, for example, be "Zero All", meaning that the "Zero All" function is associated with the upper left hand button "BUT 1". A healthcare worker may get used to pressing the upper left hand button, e.g. "BUT 1", when desiring to invoke the "Zero All" function when the device 2 is in the normal, or uninverted, orientation. In FIG. 3a, button 24 "BUT 8" is on the upper left side of the device 2. However, in FIG. 3a, the label associated with the button "BUT 8" is "LAB 1". That is, the label, and consequently the function, associated with the upper left hand button "BUT 8" is still "LAB 1". Continuing the example above, the label and function "Zero All" is associated with the button "BUT 8". This means that the upper left hand button, e.g. "BUT 8", is still associated with the function "Zero All". The same applies to the remaining labels 26 and functions associated with the associated user selectable buttons 24. This decreases the confusion and possibility of error by a healthcare worker who desired to invoke, for example, the "Zero All" function.

Similarly, FIG. 3b corresponds to the embodiment illustrated in FIG. 2. The image displayed in FIG. 2 is upright, and the label "LAB 1" is displayed within the button 24 in the upper left hand corner of the device 2. Continuing the above example, in an actual embodiment, that label may be "Zero All". By pressing that touch screen button 24, the user invokes, for example, the "Zero All" function. The image displayed in FIG. 3b is also upright, and the label "LAB 1" is displayed within the button in the upper left hand corner, even though the device is in the inverted orientation. Continuing the above example, in an actual embodiment, that label may be "Zero All". By pressing that touch screen button 24, the user invokes, for example, the "Zero All" function.

Thus, in both the uninverted (FIG. 1 and FIG. 2) and the inverted (FIG. 3a and FIG. 3b) orientations, the image 22 is displayed in an upright orientation on the display screen 20 of the device 2. The medical parameters, both graphic and textual, are displayed in an upright manner providing easy and accurate interpretation by healthcare workers. In addition, the buttons 24 and associated labels 26 are maintained in the same configuration so that the button in the same relative location, e.g. upper left hand button, is associated with the same label and the same function in both orientations. The minimizes confusion of and potential errors by the healthcare worker.

As described above, the one or more cables 5 convey patient data, and in particular patient physiological signals, from patient attached sensors (not shown) to the device 2. The first orientation (FIG. 1 and FIG. 2) and second orientation (FIG. 3a and FIG. 3b) correspond to different locations of the device 2 relative to a patient. In the different locations, the particular side of the device 2, e.g. side 4, is proximate to the patient, enabling substantially direct routing of the one or more cables 5 from the device 2 to the patient. More specifically, the different locations of the device 2 relative to the patient are positions on either side of the patient.

For example, the device 2 may be mounted on a movable bed or gurney, and in particular may be mounted on the headboard of the gurney. The device 2 is oriented in such a manner that the side 4 to which the cables 5 are attached is facing the inside of the gurney. This minimizes potential tangling or snaring of the one or more cables 5 on external obstructions as the gurney is transported from room to room. Assume a patient is lying on the gurney, and the device 2 is mounted on the headboard of the gurney. If the device 2 is mounted on the left side of the headboard, then the device 2 is oriented so that the particular side 4 is on the right side, proximal to the patient, enabling substantially direct routing of the cables 5 from the device 2 to the patient. This is the orientation illustrated in FIG. 1 and FIG. 2. Similarly, if the device 2 is mounted on the right side of the headboard, then the device 2 is oriented so that the particular side 4 is on the left side, proximal to the patient, enabling substantially direct routing of the cables 5 from the device 2 to the patient. This is the orientation illustrated in FIG. 3a and FIG. 3b.

Referring to FIG. 1, as described above, in one embodiment an input processor 50 receives user entered data selecting an image orientation and overriding the sensor 10 detected orientation. By supplying user data to the input processor 50, a user may manually select a desired orientation which may be different from the orientation detected by the orientation sensor 10 and represented by the orientation signal 12.

Figure 4:
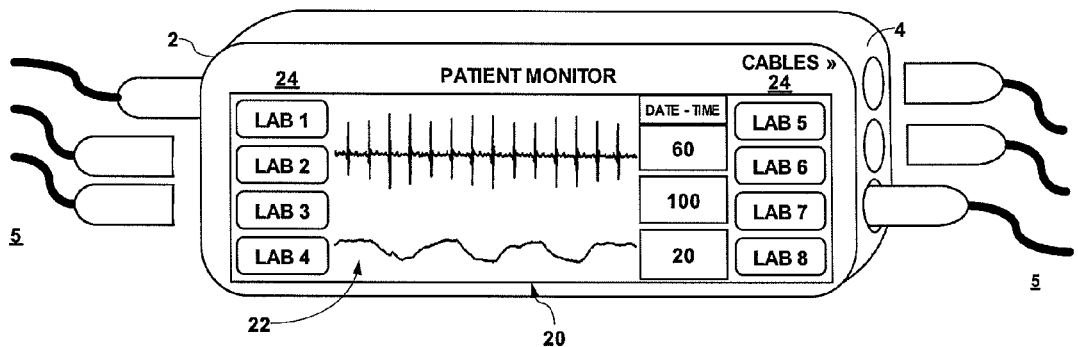
FIG. 4 is a diagram in orthogonal form illustrating a portion of another embodiment of a system according to principles of the present invention.

In the description above, the device 2 is illustrated as supporting connection of one or more cables 5 on one side 4 of the device 2. One skilled in the art understands that the device 2 may be configured to support connection of the one or more cables 5 on both opposite sides of the device 2, as illustrated in FIG. 4. In this embodiment, the orientation sensor 10 may detect the orientation of the device 2 in response to the detection of the side on which the one or more cables 5 are conveying data. Further, the device 2 is illustrated as being rectangular and wider than it is high. One skilled in the art understands that the device may be higher than it is wide, or be more nearly square with substantially the same width and height, or any other shape. In addition, fewer or more medical parameters may be displayed on the display screen 20 of the device 2, and any number of cables 5 may be included to gather physiological signals required to generate the medical parameters.

What is claimed is:

1. A system for adaptively orienting a display image on a device for presenting data acquired via one or more cables carrying physiological data connected to a particular side of said device, comprising:
   at least one connector positioned on said particular side of said device for connection of the one or more cables;
   a sensor for detecting orientation of said device and providing a device orientation representative signal indicating whether said device is in a first orientation or a second orientation substantially different to said first orientation, said sensor detecting a change in orientation of said device between said first orientation and said second orientation to enable substantially direct routing of said one or more cables;
   a display screen for presenting display images on said device;
   a plurality of user selectable physical buttons positioned on opposing sides of said display screen;
   a display generator for automatically generating a display image on said display screen oriented to be upright in said first and second orientations of said device, in response to said orientation representative signal; and
   a command processor for adaptively selecting functions assigned to each of said plurality of user selectable physical buttons, said buttons and associated labels are maintained in a same configuration where, in both said first and second orientations, a button in a same relative location with respect to said display image is associated with a same label and function in response to said orientation representative signal.

2. A system according to claim 1, including an input processor for receiving user entered data selecting an image orientation and overriding said sensor detected orientation.

3. A system according to claim 1, wherein said sensor detects orientation of said device in response to detection of a position at which said one or more cables carrying physiological data are connected to said device.

4. A system according to claim 1, wherein said orientation sensor senses rotation of said device around three axes.

5. A system according to claim 4 wherein said orientation sensor processes sensed rotation around at least two of said three axes to provide said orientation representative signal indicating whether said device is in said first or second orientation.

6. A system according to claim 1, wherein said second orientation is at least one of: (a) substantially upside down relative to said first orientation, and (b) rotated substantially 180 degrees relative to said first orientation.

7. A system according to claim 1, wherein said user selectable physical buttons are substantially symmetrically positioned on both sides of said display screen.

8. A system according to claim 1, wherein: said one or more cables convey patient data from patient attached sensors; and said first orientation and second orientation correspond to different locations of said device relative to a patient and in said different locations said particular side of said device is proximate to said patient enabling substantially direct routing of said one or more cables from said device to said patient.

9. A system according to claim 8, wherein said different locations of said device relative to said patient comprise positions on either side of said patient.

10. A system according to claim 1, wherein said functions are associated with a button positioned at a predetermined location with respect to the display image irrespective of an orientation of said device.

11. A method for adaptively orienting a display image on a device including a display screen, at least one connector positioned on a particular side of said device and a plurality of user selectable physical buttons positioned on opposing sides of the display screen for presenting data acquired via one or more cables carrying physiological data connected to said at least one connector, comprising:

detecting the orientation of said device and providing a device orientation representative signal indicating whether said device is in a first orientation or a second orientation substantially different to said first orientation, wherein detecting a change in orientation of said device between said first orientation and said second orientation enables substantially direct routing of the one or more cables that carry the physiological data and are connected to the at least one connector;

presenting display images on the display screen of said device;

automatically generating a display image oriented to be upright in said first and second orientations of said device, in response to said orientation representative signal; and adaptively selecting functions assigned to each of the plurality of user selectable physical buttons positioned on both sides of said display screen of said device such that the buttons and associated labels are maintained in a same configuration where, in both said first and second orientations, a button in a same relative location with respect to the display image is associated with a same label and function in response to the orientation representative signal.

12. The method according to claim 11, wherein said functions are associated with a button positioned at a predetermined location with respect to the display image irrespective of an orientation of said device.

* * * * *